United States Patent [19]

Ninomiya et al.

[11] Patent Number: 4,880,819
[45] Date of Patent: Nov. 14, 1989

[54] 4-AMINOPYRIDINE DERIVATIVES FOR IMPROVING IMPAIRED BRAIN FUNCTION

[75] Inventors: Kunihiro Ninomiya; Ken-Ichi Saito, both of Machida; Shuji Morita; Akihiro Tobe, both of Yokohama; Issei Nitta, Machida, all of Japan

[73] Assignee: Mitsubishi Kasei Corporation, Tokyo, Japan

[21] Appl. No.: 242,333

[22] Filed: Sep. 9, 1988

[30] Foreign Application Priority Data

Sep. 17, 1987 [JP] Japan .................... 62-233350

[51] Int. Cl.$^4$ .................. A61K 31/445; A61K 31/44; C07D 401/14; C07D 401/12
[52] U.S. Cl. .................. 514/316; 514/318; 514/343; 546/187; 546/193; 546/281
[58] Field of Search ............ 546/281, 193, 187; 514/316, 318, 343

[56] References Cited

U.S. PATENT DOCUMENTS 4,341,790 7/1982 Betzing et al. .................. 546/281 X
4,562,197 12/1985 Snarey et al. .................. 546/281 X

FOREIGN PATENT DOCUMENTS 0115472 8/1984 European Pat. Off. .
1588082 4/1981 United Kingdom .

Primary Examiner—Richard A. Schwartz
Attorney, Agent, or Firm—David G. Conlin

[57] ABSTRACT

Novel 4-aminopyridine derivatives represented by the general formula (I):

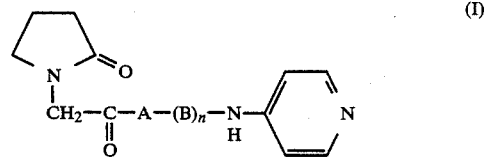

wherein A and B independently represent

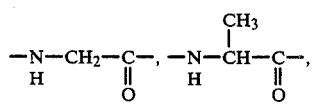

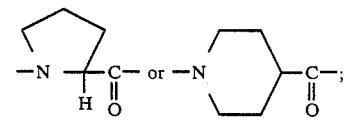

and n is an integer of 1 or 2; as well as their pharmaceutically acceptable acid addition salts are disclosed herein. The novel compounds are useful as the agent for improving impaired brain function.

2 Claims, No Drawings

4-AMINOPYRIDINE DERIVATIVES FOR IMPROVING IMPAIRED BRAIN FUNCTION

FIELD OF THE INVENTION

The present invention relates to novel 4-aminopyridine derivatives and their acid addition salts useful as agents for improving impaired brain function.

BACKGROUND OF THE INVENTION

For the treatment of the impairment of memory by different causes such as multiple infarcted dementia, senile dementia, Alzheimer's dementia, sequelae of cerebral injury and cerebral apoplexy and the like, various agents such as cerebral vasodilators, agents for improving cerebral metabolism, nootropic agents and the like have been proposed, but the satisfactory improvement could not be obtained by any of these agents.

As the extensive research with respect to the compounds showing the satisfactory improvement of the impaired brain function, the present inventors found that 4-aminopyridine derivatives in which the amino group is replaced with [(2-oxo-1-pyrrolidinyl)-acetyl]-peptide side chain improve the impaired brain function.

SUMMARY OF THE INVENTION

The present invention provides 4-aminopyridine derivatives represented by the gereral formula (I):

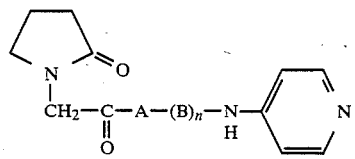
(I)

wherein A and B independently represent

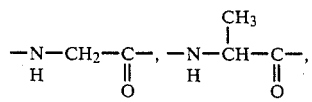

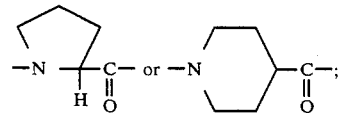

and n is an integer of 0 or 1; and their pharmaceutically acceptable acid addition salts.

And, the present invention provides the pharmaceutical composition useful as the agent for improving impaired brain function which comprises as the effective ingredient at least one of 4-aminopyridine derivatives having the general formula (I) and their pharmaceutically acceptable acid addition salts.

DETAILED DESCRIPTION OF THE INVENTION

4-Aminopyridine derivatives according to the present invention (hereinafter referred to as "the present compound(s)") have the general formula (I).

A and B in the general formula (I) independently represent

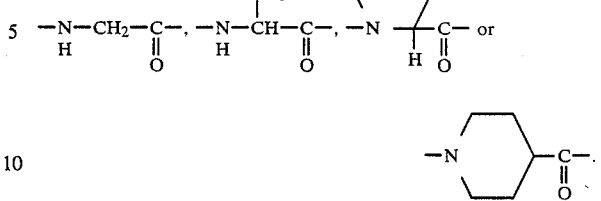

Preferably A represents —NH—CH$_2$—CO— or —NH—CH(CH$_3$)—CO—.

n in the general formula (I) is an integer of 0 or 1.

The following compounds are exemplified as the preferable present compounds.

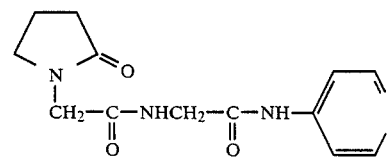

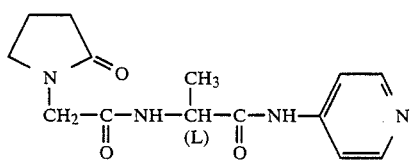

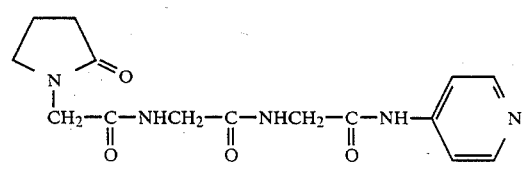

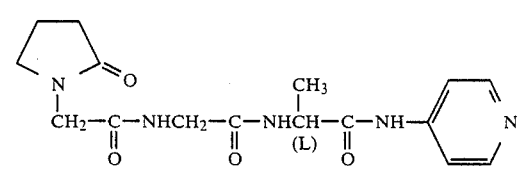

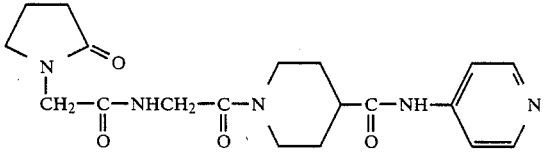

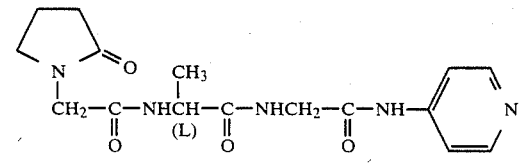

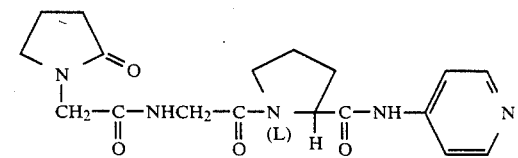

The present compounds include the pharmaceutically acceptable acid addition salts of 4-aminopyridine derivatives having the general formula (I). Their acid addition salts may be salts with inorganic acids such as hydrochloric acid, hydrobromic acid, sulfuric acid, phosphoric acid and the like, or salts with organic acids such as methanesulfonic acid, p-toluenesulfonic acid, benzenesulfonic acid, acetic acid, glycolic acid, glucronic acid, maleic acid, fumaric acid, oxalic acid, ascorbic acid, citric acid, salicylic acid, nicotinic acid, tartaric acid and the like.

The present compounds having the general formula (I) can be prepared according to any of the known methods. For example, the following methods are illustrated.

(a) n=0

(2-oxo-1-pyrrolidinyl)acetic acid is subjected to the amidation with the amine having the general formula (II)

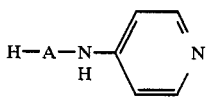
(II)

wherein A is as defined above; in the presence of the peptide condensing agent so as to prepare the present compound.

Alternatively, (2-oxo-1-pyrrolidinyl)acetic acid is converted to the reactive derivative thereof followed by subjecting to the amidation with the amine having the above general formula (II) so as to prepare the present compound.

(b) n=0 or 1

The carboxylic acid having the general formula (III)

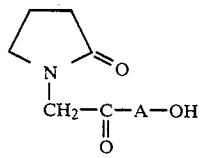
(III)

wherein A is as defined above; is subjected to the amidation with the amine having the general formula (IV)

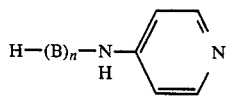
(IV)

wherein B and n are as defined above; in the presence of the peptide condensing agent so as to prepare the present compound.

Alternatively, the carboxylic acid having the above general formula (III) is converted to the reactive derivative thereof followed by subjecting to the amidation with the amine having the above general formula (IV) so as to prepare the present compound.

In the present invention, any of the conventional peptide condensing agents in the standard peptide synthesis can be used. The use of dicyclohexylcarbodiimide, carbonyldiimidazole or 1-ethoxycarbonyl-2-ethoxy-1,2-dihydroquinoline is preferable.

Examples of the reactive carboxylic acid derivatives include the mixed acid anhydride with carbonic acid monoalkylester (e.g. D—O—CO—CH$_2$CH(CH$_3$)$_2$), carboxylic acid azide (D—N$_3$), p-nitrophenyl ester

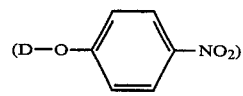

and pentachlorophenyl ester

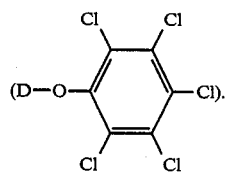

Herein, D represents

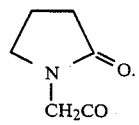

in the process (a) and

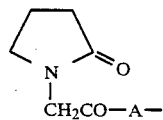

in the process (b).

Generally, the amidation is carried out in the suitable solvent under the atmospheric pressure.

The temperature in the amidation depends on the natures of the peptide condensing agent used or the reactive carboxylic acid derivative, but gererally it is in the range of $-30°$ C. to $+150°$ C.

The amines having the general formulae (II) and (IV) as well as the carboxylic acid having the general formula (III) which are used as the starting material for preparing the present compound can be prepared according to any of the known methods, for example, the methods described in the following reference examples.

The present compounds are pharmaceutically active and valuable. Especially, the present compounds have the protective actions against the amnesia caused by the electroconvulsive shock and against the behavioral disturbance induced by the administration of sodium nitrite.

Accordingly, the present compounds are useful as the agent for treating the impairment of memory by different causes such as multiple infarcted dementia, senile dementia, Alzheimer's dementia and the like and the sequelae of cerebral injury and cerebral apoplexy and the like. The pharmaceutical activities of the present compounds are higher than those of the so-called nootropic agents such as picracetam and aniracetum, as shown in the following test examples.

The present compound may be used alone for such a treatment. Preferably, the present compound is combined with the pharmaceutically acceptable carrier. That is, the pharmaceutical composition according to the present invention comprises at least one of the present compounds together with the pharmaceutically acceptable carrier and if necessary one or more of the known additives.

The pharmaceutical composition may have any of the conventional dosage forms depending on chemical properties including solubility of the compounds, administration route, administration plan and the like. For example, for the parenteral administration such as intramuscular injection, intravenous injection and subcutaneous injection, the present composition is used in the form of the sterile solution in which the solute such as salt, glucose and the like are added for obtaining the isotonic solution. For the oral administration, the present composition is used in the form of tablet, capsule or granule in which suitable vehicle such as starch, lactose, sucrose and the like is contained. Alternatively, the present composition may be used for the oral administration in the form of the troch such as rotula, lozenge and the like which is formed by adding sucrose, syrup, perfume, colouring material and so on and shaping. Alternatively, the present composition may be used for the oral administration in the form of the solution in which generally colouring material and perfume are added.

The dosage of the present compound is determined by the doctor considering the administration route, the nature of the compound and the conditions of the patient. Generally, the daily dosage via parenteral administration is 0.1 to 50 mg/kg, preferably 0.2 to 20 mg/kg; and the daily dosage via oral administration is 0.5 to 500 mg/kg, preferably 1 to 100 mg/kg.

EXAMPLES

The invention will now be further described by the following, non-limiting examples.

Example 1

Preparation of 4-{N-[(2-oxo-1-pyrrolidinyl)acetyl]-glycylamino}pyridine 40.9 g of (2-oxo-1-pyrrolidinyl)acetic acid was dissolved in 300 ml of dimethylformamide and the solution was cooled to 0° C. Then, a solution of 78.7 g of dicylohexylcarbodiimide dissolved in 80 ml of dimethylformamide was added thereto while maintaining the temperature at −2° C. to +1° C. After stirring for 5 minutes, 28.8 g of 4-(glycylamino)pyridine dissolved in 50 ml of dimethylformamide was added while maintaining the temperature at 0° to 3° C. and then the reaction liquid was allowed to stand so as to rise its temperature to room temperature over 2 hours. The liquid was cooled with ice and 200 ml of ice water was added dropwise thereto. The precipitated dicyclohexylurea was filtered off and the solvent was distilled off under reduced pressure. 200 ml of ethanol was added to the residue and stirred and the insoluble matter was filtered off. This insoluble matter was dissolved in 130 ml of water and 50 ml of methanol with warming and then the solution was concentraterd to about 60 ml. After 300 ml of ethanol was added, again the solution was concentrated to about 100 ml and allowed to stand overnight to form the precipitate, which was filtered off to obtain the titled compound.

Yield=38.8 g

Melting point=243° to 245° C.

Reference Example 1

Preparation of 4-(glycylamino)pyridine (the starting amine used in Example 1)

36 g of N-benzyloxycarbonyl glycine was dissolved in 400 ml of dimethylformamide and the solution was cooled to −8° C., to which 56.8 g of dicylohexylcarbodiimide dissolved in 50 ml of dimethylformamide was added while maintaining the temperature at −8° to −6° C. After stirring at −6° to −3° C. for 15 minutes, 17 g of 4-aminopyridine was added at −3° to −1° C. The reaction liquid was allowed to stand so as to rise its temperature to room temperature over 2 hours and stirred at room temperature overnight. Then, dicyclohexylurea was filtered off and dimethylformamide was distilled off under reduced pressure. The residue was purified through the chromatography on silica gel (silica gel 1 kg; chloroform-methanol (3%→6%) as the eluent) and recrystallized from methanol-ethyl acetate to obtain 35.2 g of 4-[(N-benzyloxycarbonyl glycyl)amino]pyridine having the melting point of 154° to 156° C. This was dissolved in 1 l of methanol and 2.3 g of palladium black was added thereto followed by subjecting to the catalytic hydrogenation at room temperature and under atmospheric pressure. After 5 hours, the catalyst was filtered off and the filtrate was concentrated to about 50 ml. 200 ml of ethyl acetate was added and again the resultant solution was concentrated to about 60 ml so as to obtain the precipitate, which was allowed to stand overnight and filtered to obtain the titled compound.

Yield=17,8 g

Melting point=134° to 137° C.

Examples 2 to 4

The following compounds (Table 1) were prepared according to the method similar to Example 1.

TABLE 1

| Example No. | structure | melting point |
|---|---|---|
| 2 | 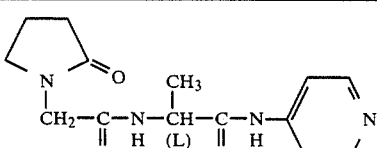 | amorphous solid |
| 3 | 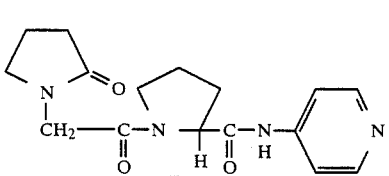 | 173~175° C. (maleic acid salt) (1:1) |

TABLE 1-continued

| Example No. | structure | melting point |
|---|---|---|
| 4 | (pyrrolidinone)-CH₂-C(=O)-N(piperidine)-C(=O)-NH-(4-pyridyl) | 225~226.5° C. |

Example 5
Preparation of 4-{N-[(2-oxo-1-pyrrolidinyl)acetyl]-glycylglycylamino}pyridine 9.01 g of N-[(2-oxo-1-pyrrolidinyl)acetyl]glycine was dissolved in 160 ml of dimethylformamide and the solution was cooled to −13° C., to which 10.32 g of dicyclohexylcarbodiimide dissolved in 15 ml of dimethylformamide was added at −13° to −10° C. After stirring at −10° C. for 30 minutes, 4.53 g of 4-(glycylamino)-pyridine was added at −10° to −8° C., which was stirred at −10° to −5° C. for 2 hours and 200 ml of methanol was added while maintaining the temperature at −5° to 0° C. The reaction liquid was allowed to stand so as to rise its temperature to room temperature over 2 hours and then methanol was distilled off under reduced pressure and the precipitated crystal was filtered off. This crystal was extracted with 20 ml of methanol and 100 ml of water, the insoluble matter was filtered off and the filtrate was concentrated to about 15 ml, to which 150 ml of ethanol was added and again the solution was concentrated to about 30 ml, allowed to stand and filterd to obtain 8.1 g of the crude crystal. This was dissolved in 20 ml of water and 200 ml of ethanol with warming and the resultant solution was concentrated to about 40 ml and allowed to stand and the crystal was filterd to obtain the titled compound.

Yield=6.14 g
Melting point=250° to 253° C.
Reference Example 2
Preparation of N-[(2-oxo-1-pyrrolidinyl)acetyl]glycine (the starting carboxylic acid used in Example 5)

55 g of (2-oxo-1-pyrrolidinyl)acetic acid was dissolved in 1 l of dimethylformamide and 39.3 g of triethylamine was added thereto. After the solution was cooled to −8° C., 55.1 g of isobutyl chloroformate was added at −8° to −1° C. Then the reaction liquid was stirred at 0° to −7° C. for 10 minutes, 50.7 g of glycine methyl ester hydrochloride was added at −7° to −4° C. and stirred at −4° to −8° C. for 6 minutes. Next, 40.8 g of triethylamine was added at −8° to −3° C. The reaction liquid was allowed to stand so as to rise its temperature to room temperature over 2 hours and triethylamine hydrochloride was filtered off. Dimethylformamide was distilled off under reduced pressure and the residue was purified through the chromatography on silica gel (silica gel 1200 g, chloroform-1 to 3% of methanol as the eluent) to obtain 70.5 g of N-[(2-oxo-1-pyrrolidinyl)acetyl]glycine methyl ester as the oily substance. This was dissolved in 120 ml of methanol and 21.7 g of potassium hydroxide dissolved in 150 ml of methanol was added thereto. After reacting at room temperature for 5 hours, 40 g of acetic acid was added. The solvent was distilled off under reduced pressure and the residue was purified through the chromatography on silica gel (silica gel 1 kg, chloroform-5 to 20% of methanol-1% of formic acid as the eluent) and crystallized from tetrahydrofuran to obtain the titled compound.

Yield: 57.2 g
Melting point: 153° to 155° C.
Examples 6 to 9
The following compounds (Table 2) were prepared according to the method similar to Example 5.

TABLE 2

| Example No. | structure | melting point |
|---|---|---|
| 6 | (pyrrolidinone)-CH₂-C(=O)-NH-CH₂-C(=O)-N(H)-CH(CH₃)-C(=O)-NH-(4-pyridyl) (L) | 237~241° C. |
| 7 | (pyrrolidinone)-CH₂-C(=O)-NH-CH₂-C(=O)-N(pyrrolidine-2-carbonyl)-NH-(4-pyridyl) (L) | 167~170° C. |

TABLE 2-continued

| Example No. | structure | melting point |
|---|---|---|
| 8 | (structure: pyrrolidinone-CH₂-C(=O)-N(H)-CH₂-C(=O)-N(piperidine)-C(=O)-N(H)-pyridine) | 273~275° C. |
| 9 | (structure: pyrrolidinone-CH₂-C(=O)-N(H)-CH(CH₃)(L)-C(=O)-N(H)-CH₂-C(=O)-N(H)-pyridine) | 271~273° C. |

Test Example 1

Effect on memory impairment

The test was carried out in accordance with the method of Susan J. Sara (Please see Psychopharmacology, 68, pages 235 to 241, 1980).

As the test device, the so-called two compartment avoidance box was used. This device comprises the lighted big box and the dark small box which is comminicated to the big box and has the metal grid floor capable of applying the foot shock.

As the experimental animal, the Wistar male rats (170 to 220 g) were used.

If the animal is entered in the big box, the animal has the tendency to immediately enter into the small box. When the animal entered in the small box, the door was closed and then the electric current was passed through the metal grid (3 mA, 5 seconds). If the same animal was entered in the big box 3 or more hours later, the animal entered into the small box not immediately, but very later. That is, the latency until the animal enters from the big box into the small box was prolonged. This reaction is generally called as "passive avoidance response".

After the electric current was passed through the metal grid and then the electroconvulsive shock was given to the animal by passing the electric current through the electrodes put on both ears of the animal (60 mA, 200 Hz, 0.8 second), the passive avoidance response was checked 3 or more hours later. The reduction in latency was observed. This reduction in latency is due to the forgetting of the electric stimulus by giving the electroconvulsive shock and it is used as the index of the impairment of memory.

Further, after the electroconvulsive shock was given and then the compound to be tested (the present compounds and the nootropic agents) was orally administrated so as to improve the impairment of memory, the passive avoidance response was checked 3 or more hours later, again. The prolongation of the latency reduced by electroconvulsive shock was observed by administrating each compound and it is used as the index of the improvement of the impairment of memory.

The improvement (%) using each compound was calculated from the following equation:

$$\text{improvement (\%)} = \frac{T - I}{C - I} \times 100$$

wherein C is latency to enter the small box in the control group;

I is latency to enter the small box in the impaired group; and

T is latency to enter the small box in the treating group.

The results are shown in Table 3.

TABLE 3

| compound (Example No.) | improvement (%) | dose (mg/kg, P.O.) |
|---|---|---|
| 1 | 24 | 10 |
|   | 21 | 30 |
|   | 39 | 100 |
| 7 | 29 | 1 |
|   | 26 | 3 |
|   | 28 | 10 |
| 9 | 54 | 10 |
|   | 59 | 30 |
|   | 52 | 100 |
| Piracetam | 22 | 250 |
|   | 14 | 500 |
| Aniracetam | 0 | 30 |
|   | 0 | 60 |
|   | 21 | 100 |

Test Example 2

Effect on NaNO₂ induced behavioral disturbance in the tight rope test

The test was carried out in accordance with the method of Gary E. Gibson (please see Pharmacology, Biochemistry & Behavior, 18, pages 909 to 916, 1983).

As the experimental animal, the ddy male mice (20 to 25 g, 6 mice per group) were used.

Firstly, the animals in the control group were subjected to the tight rope test. The tight rope test was carried out as follows. The rope having the diameter of about 2 mm and the length of about 60 cm was stretched tightly between the poles having the height of about 40 cm. The animal was held on the middle of the rope with the forelimbs and the time till the animal arrives to any pole was determined. The time limit is set within 1 minute. And, the behavior during the course was observed so as to score according to Gibson method above.

Next, 150 mg/kg of sodium nitrite was intraperitoneally administered and 30 minutes later the animmal was subjected to the tight rope test. It has been known that the animal was caused to be the anemic hypoxia and have the lowered capacity of acetylcholine synthesis by administrating sodium nitrite, thereby the score on the tight rope test being lowered.

After the administration of sodium nitrite, 30 minutes later the compound to be tested (the present compounds and the nootropic agents) was orally administered so as to improve the lowered capacity of acetylcholine synthesis and possibly the impaired brain function and further 30 minutes later the animal was subjected to the tight rope test, again. The increase with respect to the score was observed by administrating each compound.

The improvement (%) using each compound was calculated from the following equation:

$$\text{improvement (\%)} = \frac{T - I}{C - I} \times 100$$

wherein
C is the mean score in the control group;
I is the mean score in the impaired group; and
T is the mean score in the treating group.
The results are shown in Table 4.

TABLE 4

| compound (Example No.) | improvement (%) | dose (mg/kg, P.O.) |
|---|---|---|
|  | 46 | 10 |
| 1 | 38 | 30 |
|  | 20 | 100 |
|  | 56 | 3 |
| 2 | 45 | 10 |
|  | 14 | 30 |
|  | 34 | 10 |
| 5 | 55 | 30 |
|  | 27 | 100 |
|  | 56 | 10 |
| 6 | 36 | 30 |
|  | 0 | 100 |
|  | 32 | 10 |
| 8 | 61 | 30 |
|  | 55 | 100 |
|  | 21 | 10 |
| 9 | 7 | 30 |
|  | 22 | 100 |
|  | 15 | 30 |
| Piracetam | 30 | 100 |
|  | 39 | 300 |
|  | 51 | 30 |
| Aniracetam | 8 | 100 |
|  | 0 | 300 |

EFFECT OF THE INVENTION

The present compounds are useful as the agents for improving the impaired brain function.

What is claimed is:

1. A 4-Aminopyridine derivative represented by the formula (I):

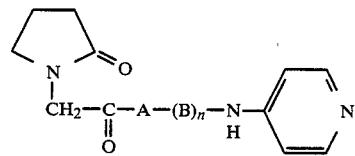

wherein A and B independently represent

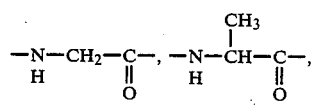

and n is an integer of 0 or 1; or a pharmaceutically acceptable acid addition salt thereof.

2. A pharmaceutical composition useful as an agent for improving impaired brain function comprising as the effective ingredient a 4-aminopyridine derivative represented by the formula (I):

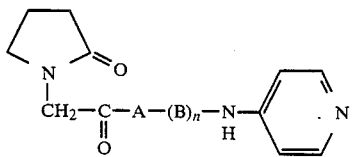

wherein A and B independently represent

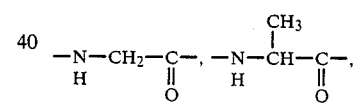

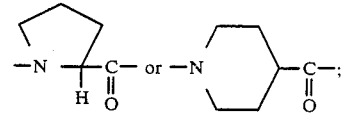

and n is an integer of 0 or 1; or its pharmaceutically acceptable acid addition salt and a pharmaceutically acceptable carrier therefor.

* * * * *